(12) United States Patent
Upadhyayula et al.

(10) Patent No.: US 11,192,917 B2
(45) Date of Patent: Dec. 7, 2021

(54) IONIC LIQUID BASED SUPPORT FOR MANUFACTURE OF PEPTIDES

(71) Applicant: INDIAN INSTITUTE OF TECHNOLOGY DELHI, New Delhi (IN)

(72) Inventors: Sreedevi Upadhyayula, New Delhi (IN); Tanmoy Patra, New Delhi (IN); Subhasis Paul, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 80 days.

(21) Appl. No.: 16/473,381

(22) PCT Filed: Dec. 28, 2017

(86) PCT No.: PCT/IN2017/050623
§ 371 (c)(1),
(2) Date: Jun. 25, 2019

(87) PCT Pub. No.: WO2018/122874
PCT Pub. Date: Jul. 5, 2018

(65) Prior Publication Data
US 2020/0140480 A1    May 7, 2020

(30) Foreign Application Priority Data
Dec. 28, 2016   (IN) .............. 201611044691

(51) Int. Cl.
*C08F 8/32* (2006.01)
*C07K 1/04* (2006.01)
*C08F 12/18* (2006.01)

(52) U.S. Cl.
CPC ............ *C07K 1/042* (2013.01); *C08F 8/32* (2013.01); *C08F 12/18* (2013.01)

(58) Field of Classification Search
None
See application file for complete search history.

(56) References Cited

U.S. PATENT DOCUMENTS

2010/0292439 A1* 11/2010 Vaultier ............... C07K 1/04
530/341

FOREIGN PATENT DOCUMENTS

| EP | 1534734 B1 | 5/2008 |
| WO | 2008/003836 A1 | 1/2008 |

OTHER PUBLICATIONS

Chen et al (Tetrahedron Lett 53:2684-2688, 2012) (Year: 2012).*
International Search Report in International Application No. PCT/IN2017/050623.
Written Opinion of the International Search Authority in International Application No. PCT/IN2017/050623.
EP 1534734 B1_Espacenet_English Abstract.

\* cited by examiner

*Primary Examiner* — Craig D Ricci
(74) *Attorney, Agent, or Firm* — Ladas & Parry LLP

(57) ABSTRACT

The present invention relates to an ionic liquid based support of Formula-I: wherein: $X^+$ is a heteroatom containing cationic part; W is a halogen containing polymeric solid support; n is an integer in the range of 2 to 8; Y is a hydrophobic anion; R is selected from CO—Z or Z; Z is selected from the group consisting of —Cl, —Br, —OH, —O-Alkyl and combinations thereof. The present invention also relates to a process for preparation of said ionic liquid based support used for di, oligo or polypeptide manufacture.

2 Claims, 1 Drawing Sheet

IONIC LIQUID BASED SUPPORT FOR MANUFACTURE OF PEPTIDES

RELATED APPLICATION

This application is an application under 35 U.S.C. 371 of International Application No. PCT/IN2017/050623 filed on 28 Dec. 2017, which claims priority from India Application 201611044691 filed 28 Dec. 2016, the disclosures of which are incorporated in their entirety by reference herein.

FIELD OF THE INVENTION

The present invention relates to a class of functionalized ionic liquid based supports used for di, oligo or polypeptide manufacture. The present invention also relates to a process for preparation of said ionic liquid based support.

BACKGROUND OF THE INVENTION

Several support materials are reported till date for the manufacture of peptides via viable routes. These support materials are used in both homogeneous and heterogeneous phase to attach an amino acid first in presence of auxiliary reagents like dehydrating agent or activating agent. Then, the chain is grown further to form a peptide chain by adding other properly protected amino acids one by one. After the addition of the amino acids to the chain the protecting groups are removed in each step. Finally, the synthesized peptide is detached from the support in the final step. The major complications arise from the increased number of steps for protection and deprotection of the amino acids. The other drawbacks in these processes arise due to the separation issues involved in each step leading to poor overall yield. The reported support materials provide several advantages over the conventional homogeneous phase routes like easy purification of excess reagents by simple filtration and washing, easy separation of products, parallel library synthesis and automation. However, these solid supports being heterogeneous by nature have some serious disadvantages which lead to non-linear reaction kinetics, unequal distribution to the reaction site, solvation, retarded coupling, low loading capacity of the resin, and erroneous sequences accumulation together with the desired polypeptide.

US 20060149035 discloses the use of ionic liquids as solvents for the synthesis and selective biocatalytic modification of peptides, peptide mimetics and proteins. The ionic liquid was used as a solvent in the presence of a protease, peptidase and/or hydrolase, to form a peptide bond between the amino component and the carboxyl component. The ionic liquid was used as mere solvent and other functional properties of the ionic liquid was not used in the process. Also, the use of peptidase, protease and hydrolases increases the overall cost and hence, the process is not at all industrially scalable.

EP2107067 discloses a method of synthesizing a dipeptide, an oligopeptide or polypeptide where coupling of an amino acid or peptide to a second amino acid or peptide were conducted in the presence of a boron compound. The boron compound were comprised of a boron oxygen bond, which catalyzed the formation of a peptidic bond. In this method, one of the stereoisomers was found to form in excess of the other stereoisomer or stereoisomers.

US20100041869 discloses a set of ionic liquids to be used as a liquid support in peptide synthesis comprising of 2 to 30 monomer units. In this method at least one monomer was attached to the ionic liquid support followed by addition of one or more oligopeptides and detachment of the formed peptide from the ionic liquid support. The use of viscous ionic liquids retarded the kinetics and the use of auxiliary reagents increased the overall cost of the process.

US20130137853A1 and US008691941B2 discloses an ionic liquid supported di, oligo or polypeptide synthesis without the use of peptide hydrolase or any condensation agent. First, the amino acid was converted into its ionic liquid form and then further amino acids were added to the chain in presence of water not more than 20% by mass relative to the total mass of the reaction system to yield di, oligo or polypeptides at higher concentrations. The kinetics of the reaction was slow because of the highly viscous Phosphonium based ionic liquid supports and the overall reaction time for the addition of a single amino acids was as high as 3 days.

A number of research papers have been published till date in this field. In 1963, Robert Bruce Merrifield reported a solid resin like supported material as a support for the manufacture of a tetrapeptide. The resin like supported material resulted in very high overall improved yield without any major separation issues. The use of these support material resulted in several advantages like easy purification of excess reagents by simple filtration and washing, easy separation of the products, parallel library synthesis and automation. Still, this process suffers from poor loading capacity of the resins, retarded kinetics and hence slower reaction, erroneous sequence accumulation, etc.

Visser et al. reported fluorous tagged molecules for the purification of peptides. Mizuno et al. reported a homogeneous soluble polymeric support materials for the manufacture of di, oligo or polypeptides. Three different type of fluorous supports were reported to be used as support for this process. Mizuno et al. reported synthesis of new fluorous supports to prepare a peptide having a C-terminal COOH based on fluorous chemistry. Even with several advantages over SPPS and ease of purification of products, it shows some limitations such as very low loading capacity, poor automation, and alteration of solubility during synthesis of longer peptide, aqueous solubility and insolubility in ether solvent. Montanari et al. reported a new fluorous capping reagent for facile purification of peptides synthesized on the solid phase. Again, with increasing peptide chain length the solubility in fluorous phase decreases. So this method is applicable up to small peptide chain synthesis. Owing to the inherent disadvantages of the above methods, new routes for peptide synthesis need to be explored.

Erbeldinger et al. reported the first use of ionic liquids for the thermolysin catalyzed synthesis of a peptide Z-aspartame. The ionic liquid was used as a solvent for the reaction resulting in improved yield in the process and the enzyme was reported to gain stability in presence of the ionic liquid. The application of the ionic liquid was limited to a solvent only facilitating the end group attachment of amino acids for hindered peptides by controlling the puckering of the side chain.

Vallette et al. reported a process using ionic liquid as solvent for the peptide synthesis step. Use of the ionic liquids proved to be advantageous than the conventional organic solvents in terms of the unproved yield of the hindered peptide. The electrostatic interaction of the ionic liquid in controlling the puckering of the growing peptide chain makes the end group free and hence, the formation of hindered peptide becomes facile. Miao et al. reported an ionic liquid as a support for a pentapeptide synthesis in presence of dehydrating as well as activating agents. One of the major concerns in this type of reactions, the racemization of the amino acids was found to be negligible with the use of these liquid phase ionic liquid support. Again, the use of viscous ionic liquids in the process decreases the overall yield. Also, the use of auxiliary reagents like dehydrating and activating agents increases the separation issues in the process. Celine Roche et al. reported the use of onium salt in combination with ionic liquids as organic solvent soluble supports for the synthesis of smaller peptides. The inefficiency of the onium salts in controlling the growing peptide chain kinetically retarded. Also, the initial starting material as well as the use of auxiliary reagents increase the overall cost of the process.

From the list of several support materials used in the process, the use of ionic liquids have shown tremendous promises to overcome the present issues in this field. The use of ionic liquids as supports as well as solvents for the manufacture of peptides have several advantages like more control of the process by controlling the solubility and improving the separation issues, faster kinetics, no racemization issues in the reaction, etc. Still, the reported materials are not suitable for the manufacture of few typical peptides containing multiple acidic or basic functionalities where the C-terminal approach is not good enough. Many of the reported ionic liquids were comprising of very high viscosity and hence, resulted in retarded kinetics. The use of auxiliary reagents by properly tuning the ionic liquid functionality can also be minimized.

The use of N-terminal approach for the manufacture of peptides containing multiple functionality is not reported in the literature. The combination of an ionic liquid as a support and another ionic liquid as a solvent for the peptide manufacture process to get rid of the excess use of the volatile organic solvents is not reported till date. Minimizing the use of dehydrating agent and the activating agent in the process by incorporating those functionalities in the ionic liquid support itself is not reported till date.

SUMMARY OF THE INVENTION

According to one embodiment of the invention, there is provided an ionic liquid based support of Formula-I:

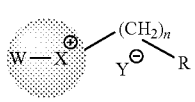

Formula-I wherein: $X^+$ is a heteroatom containing cationic part;
W is a halogen containing polymeric solid support;
n is an integer in the range of 2 to 8;
$Y^-$ is a hydrophobic anion;
R is selected from CO—Z or Z;
Z is selected from the group consisting of —Cl, —Br, —OH, —O-Alkyl and combinations thereof.

According to another embodiment of the invention, there is provided a method for the preparation of a novel ionic liquid of claim 1, comprising the steps:
  i) attaching a heteroatom containing cationic part ($X^+$) of an ionic liquid with a halogen containing polymeric solid support in an organic solvent at temperature in the range of 40° C. to 110° C. to obtain a solid product;
  ii) washing the solid product with another organic solvent to obtain a washed solid product;
  iii) subjecting the washed solid product to anion metathesis using an anionic source selected from the group consisting of methane sulfonate, triflate, hexafluorophosphate, trifluoromethanesulfonate, bistrifluoromethane sulfanimide, and tetrafluroborate or combinations thereof in a solvent under stirring conditions at a temperature ranging from 20° C. to 60° C. to obtain an anion metathesis product;
  iv) drying the metathesis product at a temperature ranging from 60° C. to 120° C. under reduced pressure in between 60 mm Hg to 20 mm of Hg to obtain ionic liquid based support.

These and other features, aspects, and advantages of the present subject matter will become better understood with reference to the following description. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The above and other features, aspects, and advantages of the subject matter will be better understood with regard to the following description and accompanying drawings where:

DETAILED DESCRIPTION OF THE INVENTION

Figure 1:
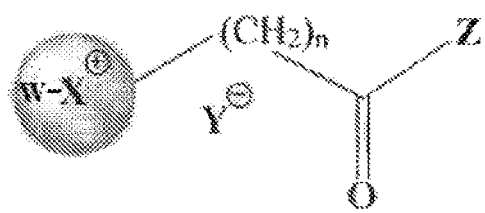
FIG. 1 shows the structure of the functionalized ionic liquid based solid support used for N-terminal approach.

The present invention relates to a class of functionalized ionic liquid used as supports as well as solvents for di, oligo or polypeptide manufacture. The present invention also relates to a process for preparation of said functionalized ionic liquids.

In one embodiment of the invention, there is provided an ionic liquid based support of Formula-I;

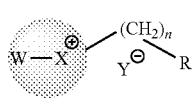

Formula-I wherein: $X^+$ is a heteroatom containing cationic part;
W is a halogen containing polymeric solid support;
n is an integer in the range of 2 to 8;
$Y^-$ is a hydrophobic anion;
R is selected from CO—Z or Z;
Z is selected from the group consisting of —Cl, —Br, —OH, —O-Alkyl and combinations thereof.

In one embodiment of the invention, there is provided an ionic liquid based support wherein R is CO—Z. In another embodiment of the invention, there is provided an ionic liquid based support wherein R is Z.

In one embodiment of the invention, there is provided an ionic liquid based support has a mesh size in the range of 10 to 70.

In one embodiment of the invention, the heteroatom containing cationic part is selected from the group consisting of imidazole, triethylamine, diethanolamine, diethyl amine, pyridine, triethanolamine, triethylphosphine and combinations thereof.

In one embodiment of the invention, the halogen containing polymeric solid support is selected from the group consisting of chloromethyl polystyrene, hydroxyethylpolystyrene, divinyl benzene crosslinked chloromethyl polystyrene and combinations thereof.

In one embodiment of the invention, the hydrophobic anion is selected from the group consisting of methane sulfonate, triflate, hexafluorophosphate, trifluoromethanesulfonate, bistrifluoromethane sulfanimide, tetrafluroborate and combinations thereof.

In one embodiment of the invention, the ionic liquid based support comprises ionic solvent. In another embodiment of the invention, ionic solvent is selected from the group consisting of triethylamine, diethanolamine, triethanolamine, diethyl amine, imidazole, triethylphosphine based functionalized ionic liquid.

In one embodiment of the invention, there is provided a method for the preparation of the ionic liquid based support, comprising the steps:
 i) attaching a heteroatom containing cationic part ($X^+$) of an ionic liquid with a halogen containing polymeric solid support in an organic solvent at temperature in the range of 40° C. to 110° C. to obtain a solid product;
 ii) washing the solid product with another organic solvent to obtain a washed solid product;
 iii) subjecting the washed solid product to anion metathesis using an anionic source selected from the group consisting of methane sulfonate, triflate, hexafluorophosphate, trifluoromethanesulfonate, bistrifluoromethane sulfanimide, and tetrafluroborate or combinations thereof in a solvent under stirring conditions at a temperature ranging from 20° C. to 60° C. to obtain an anion metathesis product;
 iv) drying the metathesis product at a temperature ranging from 60° C. to 120° C. under reduced pressure in between 60 mm Hg to 20 mm of Hg to obtain ionic liquid based support.

In one embodiment of the invention, the heteroatom containing cationic part ($X^+$) is attached with halogen containing polymeric solid support in an organic solvent selected from a group of toluene, acetonitrile, ethanol, and acetone or combinations thereof.

In one embodiment of the invention, the heteroatom containing cationic part ($X^+$) is attached with halogen containing polymeric solid support in an organic solvent at a temperature preferably in the range of 60° C. to 110° C.

In one embodiment of the invention, the side chain containing functional group is attached to the cationic part of the ionic liquid based support in an organic solvent selected from a group of toluene, acetonitrile, ethanol, acetone and combinations thereof.

In one embodiment of the invention, the side chain containing functional group is attached to the cationic part of the ionic liquid based support in an organic solvent at temperature preferably in the range of 0° C. to 50° C.

In one embodiment of the invention, the solid product is washed with organic solvent selected from the group consisting of diethyl ether, acetone, ethanol, toluene and combinations thereof.

In one embodiment of the invention, the washed solid product is subjected to anion metathesis using an anionic source selected from the group consisting of methane sulfonate, triflate, hexafluorophosphate, trifluoromethanesulfonate, bistrifluoromethane sulfanimide, and tetrafluroborate or combinations thereof in a solvent selected from the group consisting of dichloromethane, water, ethanol and combinations thereof.

In one embodiment of the invention, the washed solid product is subjected to anion metathesis using an anionic source in a solvent at a temperature in the range of 35° C. to 60° C.

In one embodiment of the invention, the metathesis product was dried under reduced pressure of less than 20 mm of Hg.

The present invention is further described in terms of N-terminal peptide synthesis approach and C-terminal peptide synthesis approach.

The structure of the ionic liquid based solid support used for the N-terminal approach has several functionalized part as shown in FIG. 1. The cationic part of the ionic liquid based solid support as mentioned as "$X^+$" contains a polymeric part selected from a group of chloromethyl polystyrene, hydroxyethylpolystyrene, divinyl benzene crosslinked chloromethyl polystyrene and combinations thereof. The ionic liquid cationic functionality in "$X^+$" is selected from a group consisting of imidazole, triethylamine, diethanolamine, diethyl amine, pyridine, triethanolamine, triethylphosphine functionality, and combinations thereof. W is a halogen containing polymeric solid support. The number "n" defining the number of C's in the side chain may be in between 1-8, preferably in between 2-6, more preferably in between 2-4. Side chain functionality "Z" for ionic liquid based supports is selected from a group of —Cl, —OH, —OCH$_3$, —OC$_2$H$_5$ and combinations thereof; the anionic species, "$Y^-$", is selected from a group of methane sulfonate, triflate, hexafluorophosphate, trifluoromethanesulfonate, tetrafluroborate, and combinations thereof.

Figure 2:
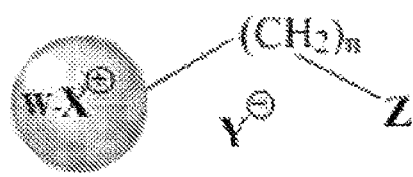
FIG. 2 shows the structure of the functionalized ionic liquid based solid support used for C-terminal approach.

The structure of the ionic liquid based solid support used for the C-terminal approach has several functionalized part as shown in FIG. 2. The cationic part of the ionic liquid based solid support as mentioned as "$X^+$" contains a polymeric part selected from a group of chloromethyl polystyrene, hydroxyethylpolystyrene, divinyl benzene crosslinked chloromethyl polystyrene and combinations thereof. The ionic liquid cationic functionality in "$X^+$" is selected from a group consisting of imidazole, triethylamine, diethanolamine, diethyl amine, pyridine, triethanolamine, triethylphosphine and combinations thereof. W is a halogen containing polymeric solid support. The number "n" defining the number of C's in the side chain may be in between 1 to 8, preferably in between 2 to 6, more preferably in between 2 to 4. Side chain functionality "Z" for ionic liquid based supports is selected from a group of —Cl, —Br, —OH and combinations thereof; the anionic species, "$Y^-$", is selected from a group of methane sulfonate, triflate, hexafluorophosphate, trifluoromethanesulfonate, tetrafluroborate and combinations thereof.

The polymeric part in the ionic liquid based support material was of mesh size in between 10 to 70, preferably in between 15 to 60 and before attaching the ionic liquid the polymeric part may contain halogen atom loading of less than 18.05 mmol per g, preferably 10.50 mmol per g, more preferably 5.50 mmol per g was used.

In the present invention the ionic liquid based solid support for the N-terminal approach method was synthesized by attaching the heteroatom containing cationic part of the ionic liquid with the solid support by removal of the halogen pan efficiently under vigorous magnetic stirring in a solvent selected from a group of toluene, acetonitrile, ethyl acetate, water, ethanol and combinations thereof at a temperature in between 40° C. to 110° C., preferably in the range of 60° C. to 110° C., more preferably in between 75° C. to 90° C. for about 8 to 36 h, preferably in between 12 to 30 h, more preferably in between 18 to 24 h. The obtained solid was filtered and washed with an organic solvent selected from a group of acetone, ethanol, methanol, and combinations thereof. Further the side chain containing functionality of the ionic liquid was attached to the obtained solid in an organic solvent selected from a group of toluene, acetonitrile, ethanol, acetone and combinations thereof at temperature in the range of 0° C. to 110° C., preferably in the range of 0° C. to 50° C. The resultant solid product was further washed using common organic solvents like diethyl ether, acetone, ethanol, toluene and combinations thereof. The anion metathesis was carried out using the anionic source anionic source selected from the group consisting of methane sulfonate, triflate, hexafluorophosphate, trifluoromethanesulfonate, bistrifluoromethane sulfanimide, and tetrafluroborate or combinations thereof, containing species in a solvent selected from a group of dichloromethane, water, ethanol and combinations thereof under stirring conditions at a temperature ranging from room temperature to 60° C., specifically in the range of 35° C. to 60° C.

In the present invention the ionic liquid based solid support for the C-terminal approach method was synthesized by attaching the heteroatom containing cationic part of the ionic liquid with the solid support by removal of the halogen part efficiently under vigorous magnetic stirring in a solvent selected from a group of toluene, acetonitrile, ethyl acetate, water, ethanol and combinations thereof at a temperature in between 40° C. to 110° C., preferably in the range of 60° C. to 110° C., more preferably in between 75° C. to 90° C. for about 8 to 36 h, preferably in between 12 to 30 h, more preferably in between 18 to 24 h. The obtained solid was filtered and washed with an organic solvent selected from a group of acetone, ethanol, methanol, and combinations thereof. Further the side chain containing functionality of the ionic liquid was attached to the obtained solid in an organic solvent selected from a group of toluene, acetonitrile, ethanol, acetone and combinations thereof at temperature in the range of 0° C. to 110° C., preferably in the range of 50° C. to 110° C. The resultant solid product was further washed using common organic solvents like diethyl ether, acetone, ethanol, toluene and combinations thereof. The anion metathesis was carried out using an anionic source containing a solvent selected from a group of dichloromethane, water, ethanol and combinations thereof under stirring conditions at a temperature ranging from room temperature to 60° C., specifically in the range of 35° C. to 60° C.

In the present invention, the ionic solvent was synthesized by attaching the heteroatom containing cationic part of the ionic liquid with the side chain containing functionality in an organic solvent selected from a group of toluene, acetonitrile, ethanol, acetone and combinations thereof at temperature in the range of 0° C. to 110° C., preferably in the range of 80° C. to 110° C. The resultant solid product was further washed using common organic solvents like diethyl ether, acetone, ethanol, toluene and combinations thereof. The anion metathesis was carried out using an anionic source containing species in a solvent selected from a group of dichloromethane, water, ethanol and combinations thereof under stirring conditions at a temperature ranging from room temperature to 60° C., specifically in the range of 35° C. to 60° C. Finally, the ionic liquid was dried at 120° C. under reduced pressure of around 10 mm of Hg.

When the above-mentioned ionic liquid was used as the active support in combination with another ionic liquid to be used as a solvent for the reaction, can be the same ionic liquid as the support or a different ionic liquid which was easy to separate from the system. The combination of the ionic liquids is such that the interaction between them do not interfere their individual function in the reaction.

Ionic liquid used as the solvent for the reaction must possess low to moderate viscosity to facilitate the fast reaction kinetics. The use of more than 20% water by volume of the reagents was not sufficient to stop the puckering effects of longer peptide chain which retards the kinetics of the reaction. The water content of the reaction was controlled by reducing the pressure in the range of 10 to 120 mm of Hg, preferably in the range of 20 to 90 mm of Hg, more preferably in the range of 30 to 60 mm of Hg.

In an embodiment of the present disclosure, there is provided an ionic liquid based support in combination with an ionic solvent for the manufacture of di, oligo or polypeptides, wherein the C-terminal or the N-terminal of the amino acids or peptides to be attached to the chain is blocked. After addition of each blocked amino acid or peptides to the growing peptide chain the blocking functionalities were removed following the conventional literature.

In an embodiment of the present disclosure, there is provided an ionic liquid based support in combination with an ionic solvent for the manufacture of di, oligo or polypeptides, wherein the used blocked amino acids or peptide combinations were selected from a group of Glycine (Gly), Leucine (Leu), Phenyl alanine (Phe-Ala), Lysine (Lys), Tryptophan (Trp), Aspartic acid (Asp) and analogues as well as oligomers and polymerized products.

The di, oligo or polypeptides manufactured using these ionic liquid based solid supports in combination with an ionic solvent can be used as artificial sweeteners, food and food additives, pharmaceutical products, useful chemical reagents, etc.

The present invention is more particularly described in the following examples, that are intended as illustrations only, since numerous modifications and variations within the scope of the present invention will be apparent to those skilled in the art. Unless otherwise noted, all parts, percentages and ratios reported in the following examples are on a weight basis and all reagents used in the examples were obtained or are available from the chemical suppliers.

EXAMPLES

The following examples are given by way of illustration of the present invention and should not be construed to limit the scope of present disclosure. It is to be understood that both the foregoing general description and the following detailed description are exemplary and explanatory only and are intended to provide further explanation of the claimed subject matter.

Example 1

Preparation of Functionalized Ionic Liquid for N-Terminal Approach

In a typical ionic liquid preparation procedure. Equimolar amount of an amine was mixed with chloromethyl polystyrene under vigorous stirring at a temperature range of 60° C. to 110° C., preferably in the range of 80° C. to 100° C. for 12 to 24 h in an organic solvent like acetonitrile. After completion of reaction the solid mass was washed with acetone three times and dried in air at 60° C. for 4 to 6 h. An equimolar amount of the solid was reacted with 3-chloropropyl chloroformate at 0° C. in acetone for 2 h. The obtained solid mass was collected by decanting acetone and finally equimolar amount of Lithium bistrifluoromethane sulfanimide was added and stirred vigorously for 2 h to obtain the ionic liquid based solid support.

After 34 h of reaction the yield of the ionic liquid was obtained to be 89% by relative molar percentage with respect to the amount of amine added initially.

Example 2

Preparation of Functionalized Ionic Liquid for C-Terminal Approach

In a typical ionic liquid preparation procedure, Equimolar amount of an amine was mixed with Chloromethyl polystyrene under vigorous stirring at a temperature range of 60° C. to 110° C., preferably in the range of 80° C. to 100° C. for 12 to 24 h in an organic solvent like acetonitrile. After completion of reaction the solid mass was washed with acetone three times and dried in air at 60° C. for 4 to 6 h. An equimolar amount of the solid was reacted with 2-bromoethanol at 110° C. in toluene for 24 h. The obtained solid mass was collected by decanting toluene and finally equimolar amount of Lithium bistrifluoromethane sulfanimide was added and stirred vigorously for 2 h to obtain the ionic liquid based solid support.

After 54 h of reaction the yield of the ionic liquid was obtained to be 82% by relative molar percentage with respect to the amount of amine added initially.

Example 3

Preparation of the Ionic Liquid Used as the Solvent

In a typical ionic liquid preparation procedure, an amine was mixed with 1-chlorobutane stirring in the range of 80° C. to 110° C., preferably in the range of 100° C. to 110° C. for 12 to 24 h in toluene. After completion of the reaction the obtained mass was washed three times with diethyl ether. Then the ionic liquid was charged with equimolar amount of Potassium tetrafluoroborate in water for 2 h and then extracted using dichloromethane. Finally, the ionic liquid was dried under vacuum (120° C., 0.01 Torr).

Example 4

Dipeptide Manufacture Via N-Terminal Approach

The reaction mixture containing L-Phenyl alanine methyl ester and ionic liquid based solid support at 1.1:1 mole ratio was charged in a peptide vessel glass reactor in the ionic liquid solvent under reduced pressure at room temperature for 2-4 h. At the end of the reaction, the solvent along with excess amino acid was first separated from the solid mass and then separated from the amino acids by extraction using dichloromethane. The ester linkage was deprotected by treating with trifluoroacetic acid and then with triethylamine. Similarly, other C-terminal blocked Glycinyl methyl ester was attached to the chain and the ester part was removed to obtain a dipeptide, L-Phe-ala-Gly, attached to the ionic liquid based solid support. Finally, the formed dipeptide can be detached from the ionic liquid support by treating with small amount of NaOH in THF and water mixture followed by acidification at pH 5.0. The products were qualitatively as well as quantitatively analyzed using a $^1$H NMR and HPLC analysis respectively.

Example 5

Dipeptide Manufacture Via C-Terminal Approach

The reaction mixture containing Boc-Leucine and ionic liquid based solid support at 1.1:1 mole ratio was charged in a peptide vessel glass reactor in the solvent ionic liquid under reduced pressure at room temperature for 2 to 6 h. At the end of the reaction, the solvent along with excess amino acid was first separated from the solid mass and then separated from the amino acids by extraction using dichloromethane. The Boc groups were eliminated from the Leucine moiety by treating with small amount of 1:1 v/v mixture trifluoroacetic acid in dichloromethane followed by acidification at pH 5. Similarly other N-terminal blocked Fmoc-Leucine was attached to the chain and the Fmoc part was removed by treating with piperidine in dichloromethane for 2 h to obtain a dipeptide attached to the ionic liquid based solid support. Finally, the formed peptide can be detached from the ionic liquid support by treating with trifluoroacetic acid and then with triethylamine. The products were qualitatively as well as quantitatively analyzed using a $^1$H NMR and HPLC analysis respectively.

Example 6

Recycling of the Ionic Liquid Support

The functionalized ionic liquid used in the process was separated from the reaction mixture after use by washing with a solvent like water and solubilizing the subsidiary materials using an organic solvent selected from a group of dichloromethane, toluene, diethyl ether, acetone, etc. The ionic liquid was further dried under normal or reduced pressure at 120° C.

Example 7

Recycling of the Ionic Liquid Solvent

The ionic liquid used as the solvent in the process was separated from the reaction mixture after use by solubilizing the subsidiary materials using an organic solvent selected from a group of dichloromethane, toluene, diethyl ether, etc. The ionic liquid was further dried under reduced pressure at 120° C.

The present invention is not limited to the embodiments discussed herein and can be embodied by various modifications within the scope of the following claims. It should be recognized that the preferred embodiments described above are exemplary only. Certain modifications and improvements will occur to the person skilled in the art upon a reading of forgoing description. It should be understood that all such modifications and improvements have been deleted herein for the sake of conciseness and readability but are properly within the scope of the following claims.

We claim:
1. An ionic liquid based support of Formula I:

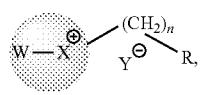

Formula-I wherein:
  X$^+$ is diethanolamine;
  W is chloromethyl polystyrene;
  n is 5;
  Y$^-$ is hexafluorophosphate; and
  R is CO—Z wherein Z is OH.

2. The ionic liquid based support as claimed in claim 1, wherein the ionic liquid based support has a mesh size in the range of 10 to 70.

\* \* \* \* \*